(12) United States Patent
Wecker et al.

(10) Patent No.: US 9,827,103 B2
(45) Date of Patent: Nov. 28, 2017

(54) FASTENING CERAMIC COMPONENTS

(71) Applicant: CeramTec GmbH, Plochingen (DE)

(72) Inventors: Heinrich Wecker, Eckental (DE);
Alfons Kelnberger, Röthenbach (DE);
Christoph Krause, Stuttgart (DE);
Frank Ziermann, Berlin (DE)

(73) Assignee: CeramTec GmbH, Plochingen (DE)

( * ) Notice: Subject to any disclaimer, the term of this patent is extended or adjusted under 35 U.S.C. 154(b) by 0 days.

(21) Appl. No.: 14/782,997

(22) PCT Filed: Apr. 7, 2014

(86) PCT No.: PCT/EP2014/056947
§ 371 (c)(1),
(2) Date: Oct. 7, 2015

(87) PCT Pub. No.: WO2014/166877
PCT Pub. Date: Oct. 16, 2014

(65) Prior Publication Data
US 2016/0030180 A1  Feb. 4, 2016

(30) Foreign Application Priority Data

Apr. 8, 2013 (DE) .................. 10 2013 005 862
Jun. 27, 2013 (DE) .................. 10 2013 212 456

(51) Int. Cl.
*A61F 2/30* (2006.01)
*A61F 2/36* (2006.01)
*A61F 2/40* (2006.01)
*A61F 2/46* (2006.01)

(52) U.S. Cl.
CPC .............. *A61F 2/30* (2013.01); *A61F 2/3609* (2013.01); *A61F 2/4014* (2013.01); *A61F 2002/30332* (2013.01); *A61F 2002/30433* (2013.01); *A61F 2002/30474* (2013.01); *A61F 2002/30604* (2013.01); *A61F 2002/365* (2013.01); *A61F 2002/3621* (2013.01); *A61F 2002/3652* (2013.01); *A61F 2002/4641* (2013.01)

(58) Field of Classification Search
CPC ................ A61F 2/36; A61F 2002/3647; A61F 2002/365; A61F 2/40; A61F 2220/0033
See application file for complete search history.

(56) References Cited

U.S. PATENT DOCUMENTS 4,227,265 A * 10/1980 Frey ...................... A61F 2/3609
403/255
4,995,883 A     2/1991 Demane et al.
(Continued)

FOREIGN PATENT DOCUMENTS

DE    43 35 931 A1    4/1995
FR    2 261 743 A2    9/1975
FR    2 310 120 A2   12/1976
(Continued)

*Primary Examiner* — Jason-Dennis Stewart
(74) *Attorney, Agent, or Firm* — Norton Rose Fulbright US LLP

(57) ABSTRACT

A ceramic component to be securely connected to an additional component in force-locked manner. A joint prosthesis comprising a ceramic sphere (1), a metallic sleeve (2) and a base plate (3) with a cylindrical projection. The connection between the ceramic sphere and the base plate or shaft (7) is secured by a screw (6).

13 Claims, 1 Drawing Sheet

(56) References Cited

U.S. PATENT DOCUMENTS

| | | | |
|---|---|---|---|
| 5,879,397 A | | 3/1999 | Kaelberer et al. |
| 2014/0222153 A1 | | 8/2014 | Bonin et al. |

FOREIGN PATENT DOCUMENTS

| | | |
|---|---|---|
| FR | 2 391 711 A1 | 12/1978 |
| FR | 2 832 625 A1 | 5/2003 |
| WO | 2012/125795 A2 | 9/2012 |

\* cited by examiner

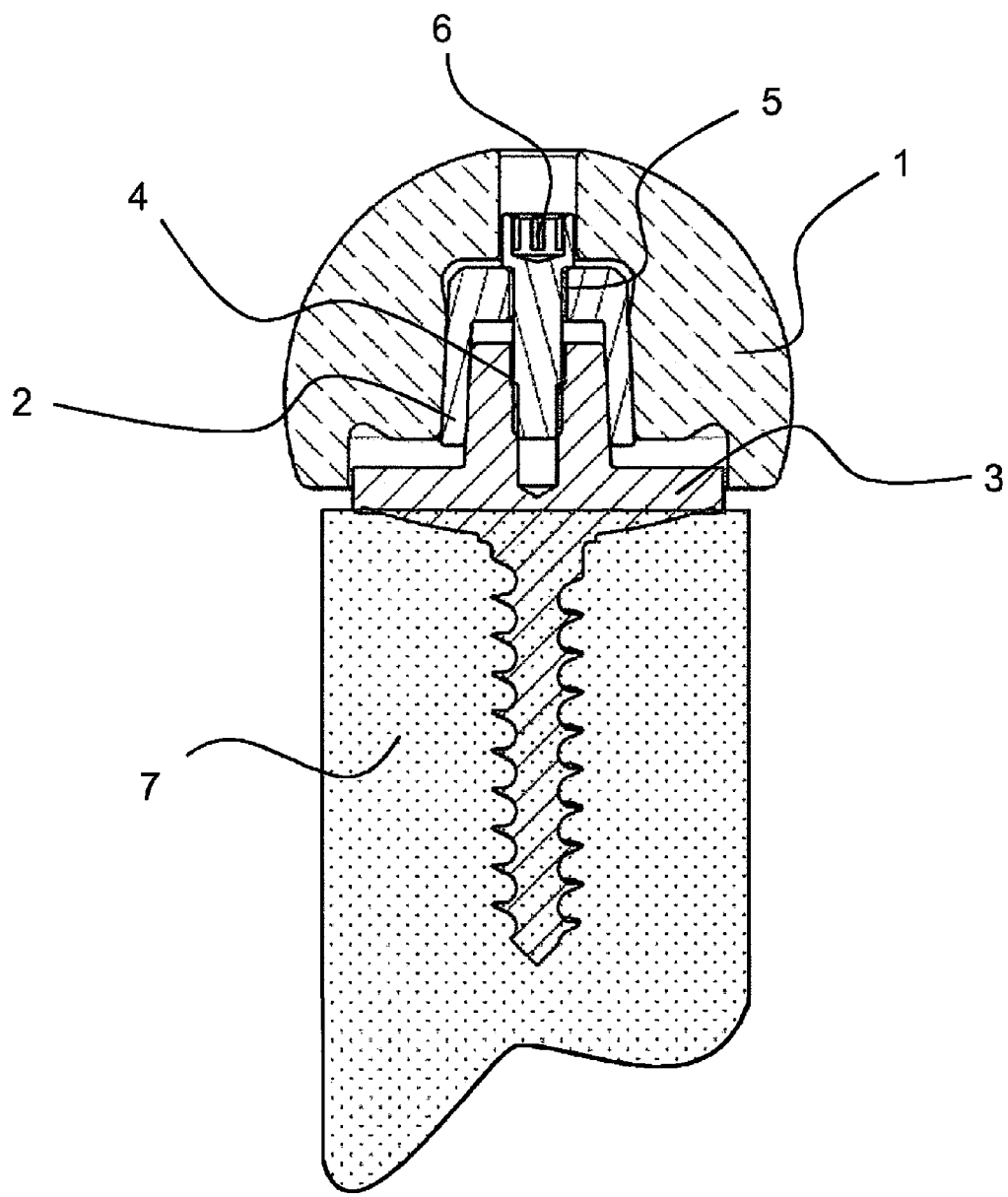

ly produced for example in the case of countersunk
FASTENING CERAMIC COMPONENTS This application is a §371 of International Application No. PCT/EP2014/056947 filed Apr. 7, 2014, and claims priority from German Patent Application Nos. 10 2013 005 862.7 filed Apr. 8, 2013 and 10 2013 212 456.2 filed Jun. 27, 2013.

FIELD OF THE INVENTION

The invention relates to fastening ceramic components to other components. In particular, the invention relates to fastening ceramic prosthetic components to other, in particular metal, prosthetic parts.

BACKGROUND OF THE INVENTION

Because of their special characteristics, components made of ceramic materials cannot, unlike for example metal components, be simply screwed to other components or be connected in a similar manner to other components. Ceramic components are very susceptible to breakage in particular in the event of point loads. For example the screwed connections exert substantial forces on the small contact areas of the pressing surface of the screw on the ceramic component. This loading can already lead to high local stresses at these contact regions and consequently to the failure of the ceramic due to fracture. Furthermore there is a notch effect at sharp edges of ceramic components such as are necessarily produced for example in the case of countersunk screws. These edges may therefore be starting points of cracks, which can in any case lead to the failure of the component in the medium term.

In particular if the ceramic components which are to be connected to other components are parts of prostheses and in particular parts of endoprostheses, such a failure of the ceramic component cannot be tolerated.

This problem is known per se. In the construction of prostheses, metal parts, in particular made of titanium and titanium alloys, are frequently used which can be screwed together without problems in order to ensure a secure connection between different components.

Ceramic components are often clamped to other components. An example of such clamping is conical clamping which is known for example from DE 43 35 931 B4. Here a ceramic component with a conical outer wall can be clamped in a metal component having a conical opening, wherein the cone of the ceramic component can have an angle different from the cone of the metal component.

The conical clamping makes possible a relatively large contact region by which point loads can be avoided. However, it has the disadvantage that the connection of the components cannot be secured against subsequent loosening. This may be problematic in particular when the ceramic component is part of a modular endoprosthesis which can only be assembled at the time of implantation into the body of the patient and of which the connection strength is dependent upon the surgeon. Such modular prostheses are used for example as hip joint or shoulder joint prostheses or also other small joint prostheses. The modular construction then comprises a stem which is for example metal and is driven into the thigh bone or the humerus. A ceramic ball is placed onto this stem as a replacement for the head of the thigh or humerus. The connection of the two components takes place by striking or impact of the head fitted onto the stem. In order to achieve a secure, non-positively engaged connection, however, the impact must take place with a precisely measured force and with a precise fit. If the fit is not optimal or the impact force is too low, the ceramic head can loosen. A secured firm connection, for example a screw connection, between the two prosthetic parts would therefore be desirable.

OBJECTS OF THE INVENTION

The object of the invention is to provide a secured, firm connection of a ceramic component to a further component.

SUMMARY OF THE INVENTION

The object of the invention is achieved by an object with the features of the.According to the present invention, a firm connection of a ceramic component to a further component comprises connection of the ceramic component to a first connecting element by means of which the connection to the further component can be produced. The connection between the ceramic component and the further component is preferably a non-positively engaged connection, in particular a screw connection. Then the connecting elements may be a male and a female part of a screw connection.

BRIEF DESCRIPTION OF THE DRAWING

FIG. 1 shows a cross-section through a hip or shoulder joint prosthesis according to the present invention.

DETAILED DESCRIPTION

In the context of the invention a firm connection is understood to be a connection which joins the ceramic component and the further component together to form a unit, so that when used correctly the unit also remains connected.

Thus in other words the invention relates to a combination of components consisting of a ceramic component and a further component which are firmly connected to one another, wherein the ceramic component is connected to a first connecting element, and the further component has a second connecting element. The connection between the ceramic component and the other component takes place exclusively by the connection of the first connecting element to the second connecting element.

Such a design is always advantageous when for example the connection of two components cannot be carried out under optimal conditions by conical clamping or when a releasable connection between the two components is required. This is the case in particular if the components are parts of a modular prosthesis, in particular a knee, hip or shoulder joint prosthesis. In the context of this invention a prosthesis is understood to be a modular prosthesis which consists of different components which particularly preferably are only assembled by the attending doctor at the time of implantation. The assembly can take place both in the body of the patient and also directly before the implantation. This has the advantage that bulky prostheses can be implanted in smaller individual parts and that the components can be assembled according to the anatomy of the patient.

According to a preferred embodiment of the invention the first connecting element can comprise a metal or a metal alloy, preferably titanium or titanium alloys.

The first connecting element can preferably be connected to the ceramic component by non-positive engagement. This non-positively engaged connection can preferably be conical clamping. According to a preferred embodiment of the invention the first connecting element can comprise a sleeve. In the context of this invention a sleeve is understood to be a cylindrical or conical body which can be hollow or solid. However, one end face of the body is closed. At least in this end face an opening is provided so that a screw or the like can be inserted therethrough and can be screwed or connected to the further component. If the body is solid, it has a through bore which leads through both end faces of the body. The opening in the end face or the bore can preferably be centered and/or provided along the axis of rotation of the body. According to another embodiment of the invention, however, an eccentric arrangement may also be advantageous in order to enable an angular arrangement between the components.

According to a modification of the invention the sleeve can comprise an internal thread into which a screw can be screwed.

According to a preferred embodiment of the invention the further component can be the stem of a prosthesis. Preferred materials for the further component comprise metals and metal alloys, in particular titanium and titanium alloys. Other materials are naturally also possible depending upon the use of the combination of components.

According to a particularly preferred embodiment of the invention, a prosthesis for hip and shoulder joints can for example comprise a ceramic head with a recess. A sleeve is fitted in non-positive engagement into the recess. The non-positively engaged fit can preferably be achieved by conical clamping of the components. However, any other non-positively engaged connection which takes account of the specific problems in the connection of ceramic materials to other materials is likewise possible.

According to a particularly preferred embodiment of the invention the sleeve can have an internal thread. If the connection between the ceramic component and the further component is designed to be releasable, the thread can be provided as a reoperation thread, that is to say it may only be used when a later replacement of the ball head becomes necessary. Then the ceramic component to be replaced, for example a prosthesis head, can be withdrawn by means of this thread from the further component, for example the prosthesis stem. This embodiment has the advantage that in the event of replacement of the ceramic component practically no mechanical load has to be exerted on the connection of the prosthesis stem to the bone. Therefore loosening of this connection also does not occur as a result of a replacement operation.

According to a further embodiment of the invention the further component comprises a second connecting element which functions as a counterpart to the first connecting element of the ceramic component. If a screw connection is provided, the second connecting element may for example be a blind hole with an internal thread when the second connecting element is designed integrally with the further component.

An embodiment is particularly preferred in which the first and the second connecting element each have a thread, but with a different thread pitch and/or thread diameter. Thus, when used correctly, securing of the components against undesirable loosening can be achieved for example by means of suitable screws. However, should a reoperation become necessary, the thread of the first connecting element can nevertheless be used as a reoperation thread.

This embodiment has the advantage that the screw is guided in a defined manner and is at a stable angle. A support surface is not necessary, and the pressing force is higher.

However, the second connecting element may also be a separate component which is firmly connected to the further component. The second connecting element may for example be a pin with or without a base plate, wherein the pin fits in positive engagement into the sleeve or the first connecting element.

The connection between the first and second connecting elements can then be produced by non-positive engagement, for example by conical clamping of the pin in the sleeve. Alternatively the pin can also have an internal thread, so that the two components can be connected by screwing.

A particularly preferred embodiment of the invention provides that the ceramic component (1) has a through opening which is aligned with an opening in the sleeve (2). In this case the opening of the sleeve has a smaller diameter than the opening of the ceramic component, so that a projecting edge of the sleeve can serve as an abutment for a fastening element, for example a screw.

If the further component of the stem is a modular prosthesis, this can have a blind hole with an internal thread. In this way the stem of the prosthesis can be driven into the bone without special consideration of the material. The ceramic ball head of the prosthesis is then fitted onto the stem and is screwed to the stem by means of a screw which is inserted into the sleeve through a hole in the ceramic head.

This has the advantage that the sleeve can serve as a guide when the head is fitted onto the stem and simultaneously as an abutment for the screw. Thus there is no direct contact of the ceramic component with the screw, so that a point loading of the ceramic component by the screw can be ruled out. Furthermore the ceramic head can be connected to the stem with a defined force and at a defined angle. This is contrary to the conventional connection of the ceramic head and the stem by means of conical clamping which is produced by impact.

A further advantage is that in the event of a component failure the ceramic head can be replaced by simple unscrewing from the stem. In contrast to the currently conventional method, in which the broken head must be broken away from the stem, with the prosthesis presented here a replacement without mechanical loading for the anchoring of the stem in the bone is possible. This advantageously prevents the loosening of the integrated stem in the bone.

A further advantage of such a connection of a ceramic component to a further component is the secured connection between the components. Such a secured connection cannot always be achieved by conical clamping. The conical clamping which is carried out by the surgeon through impacting of the head on the stem at the time of implantation has, of necessity, several uncertainty factors. On the one hand the ceramic head of the prosthesis must be struck at the correct angle, because otherwise an irregular loading of the clamping surface and thus the feared point loading of the ceramic can occur. Furthermore, an inaccurate fit also of course affects the functioning of the prosthesis. Moreover upon impact a pulse of a specific strength must act on the head, so that complete clamping occurs. Both factors, that is to say angle and pulse, are dependent upon the ability of the surgeon, and thus are prone to errors.

The invention is explained in greater detail below with reference to an embodiment of the invention. FIG. 1 shows a cross-section through a hip or shoulder joint prosthesis, which has a modular construction. A ceramic ball 1 is fitted onto a metal stem 7.

The ceramic ball 1 comprises a metal sleeve 2, wherein the sleeve is preferably made of titanium. In the factory the metal sleeve 2 is connected to the ceramic ball 1 by non-positive engagement, for example by conical clamping. The ceramic ball 1 has a through opening which is aligned with the opening in the end face of the sleeve 2. However, the opening in the end face of the sleeve 2 has a smaller diameter than the opening in the ceramic ball 1, so that the projecting upper face of the sleeve can serve as an abutment for a screw head. The opening in the ceramic ball 1 may be disposed centrally or also eccentrically.

A metal base plate 3 which has a cylindrical projection or pin with a threaded bore 4 is mounted on the stem 2. The dimensions of the sleeve 2 and of the cylindrical projection of the base plate are coordinated with one another, so that the ceramic ball 1 can be fitted by positive engagement onto the projection by means of the sleeve 2.

The connection between the ceramic ball 1 and the stem 7 is secured by a screw 5 which is screwed through the opening of the ceramic ball 1 and through the sleeve 2 into the internal thread of the cylindrical projection of the base plate 3. The projecting upper face of the sleeve 2 serves as an abutment for the screw head. Thus the non-positively engaged connection does not take place directly via the ceramic material, but to the surface of the metallic sleeve 2. Thus uncontrolled point loads on the ceramic material are avoided.

According to a preferred embodiment of the invention the sleeve 2 can likewise have an internal thread 5 which can function as a reoperation thread. The internal thread 5 advantageously has a greater diameter than the internal thread by which the ceramic component is connected properly to the other component. Then in the case of reoperation the ceramic head can be removed from the stem simply by screwing in of a larger screw without a mechanical load being exerted on the adhesion of the stem to the bone.

The advantages of the present invention are listed again below:

Secure connections are known in the hip area, but the forces which can be applied upon impact in particular cannot be transmitted to shoulder implants. The conical connection between the ceramic shoulder component and the metal stem could theoretically be sufficient, but potentially due to uncertainty of the doctor or the weaker anatomical structures it does not impact firmly enough.

In purely metal systems this insecurity has been limited by an additional securing screw between the ball head and the base—this is not possible at the interface between metal and ceramic.

The impacting and modular structure of a shoulder prosthesis is absolutely necessary for surgical reasons (orientation of the angle and the offset).

Further disadvantage: Bone cement, blood, fat, bone particles etc. in the angular gap of the conical clamping significantly reduce the strength of the ceramic component.

Proposed solution: A titanium sleeve 2 pre-pressed in the factory is firmly connected to the ceramic cone 1. This titanium sleeve 2 has a surface structure which is known and has proved successful in the hip area. In addition, it contains a thread 5 for use in the event of reoperation in the upper region. In this case a fixing screw 6 presses and centers the ceramic component 1 with the titanium sleeve 2 on the cone of the base plate 3 on a fixing thread 4.

Advantage 1: Substantially higher, defined connecting forces can be achieved by the assembly of the ceramic sleeve in the factory.

Advantage 2: No additional securing of the connection between the ceramic and the metal sleeve is necessary.

Advantage 3: The source of errors "intraoperative contamination" etc. is ruled out by the pre-assembly in the factory.

Advantage 4: No fretting (abrasion) or corrosion is possible between the sleeve and base plate made of similar material (by comparison with the solution using purely metal prostheses).

Advantage 5: By means of the reoperation thread the ball head with the titanium sleeve can be explanted by a reoperation instrument non-destructively and without loosening of the stem without in this case having to apply a striking force to the anatomical situation (compare removal of a bicycle crank).

Advantage 6: Reduction of the risk of fracture through the fixing of the ball head/titanium sleeve system on the base plate by a screw which is screwed into the fixing thread, since a direct contact of the screw head with the ceramic component can be avoided (no point loading, danger of fracture on the ceramic).

Advantage 7: Because of the poor intraoperative visibility and accessibility (anatomical location) the screw/sleeve combination serves as a guide mechanism for secure placing on the base plate.

Advantage 8: No fretting or corrosion is possible between the titanium sleeve and the ceramic.

Advantage 9: A sleeve size is compatible with all sizes and design variants of the ceramic ball and can be used universally (reducing the risk of errors during the application).

Advantage 10: The opening in the ceramic component serves as a reservoir for joint fluid (synovial fluid) for reduction of the abrasion, in particular when shells made of PE are used as parts of the joint.

It is claimed:

1. A firm connection of a ceramic component to a further component, comprising the ceramic component which is connected to a first connecting element as well as the further component with a second connecting element, wherein the connection takes place exclusively between the first and the second connecting element, bypassing the ceramic component;

wherein the first connecting element comprises a sleeve; and wherein the second connecting element comprises a metal base plate having a cylindrical projection which fits into the sleeve by positive engagement.

2. The firm connection according to claim 1, wherein the ceramic component is connected to the first connecting element by non-positive engagement.

3. The firm connection according to claim 2, wherein the ceramic component is connected to the first connecting element by non-positive engagement by conical clamping.

4. The firm connection according to claim 1, wherein the second connecting element is firmly connected to the further component.

5. The firm connection according to claim 1, wherein the connection between the ceramic component and the further component is releasable.

6. The firm connection according to claim 1, wherein the first connecting element is connected to the second connecting element by non-positive engagement.

7. The firm connection according to claim 6, wherein the first connecting element is connected to the second connecting element by non-positive engagement by conical clamping.

8. The firm connection according to claim 1, wherein the cylindrical projection has an internal thread.

9. The firm connection according to claim 1, wherein the ceramic component has a through opening which is aligned with an opening in an end face of the sleeve, wherein the opening in the end face of the sleeve has a smaller diameter than the opening of the ceramic component, so that a projecting edge of the sleeve serves as an abutment for a fastening element.

10. The firm connection according to claim 1, wherein the fastening element is a screw.

11. The firm connection according to claim 1, wherein the sleeve has an internal thread.

12. An endoprosthesis, comprising a ceramic component and a further component, wherein the ceramic component is connected to the further component by means of a firm connection according to claim 1.

13. The firm connection according to claim 1, wherein the sleeve has and opening in the end face, and wherein the opening in the end face of the sleeve has an internal thread.

* * * * *